(12) United States Patent
Holmqvist

(10) Patent No.: US 9,302,053 B2
(45) Date of Patent: Apr. 5, 2016

(54) INJECTION DEVICE

(71) Applicant: SHL Group AB, Nacka Strand (SE)

(72) Inventor: Anders Holmqvist, Värmdö (SE)

(73) Assignee: SHL Group AB, Nacka Strand (SE)

( * ) Notice: Subject to any disclaimer, the term of this patent is extended or adjusted under 35 U.S.C. 154(b) by 121 days.

(21) Appl. No.: 14/362,591

(22) PCT Filed: Nov. 28, 2012

(86) PCT No.: PCT/SE2012/051314
§ 371 (c)(1),
(2) Date: Jun. 3, 2014

(87) PCT Pub. No.: WO2013/085454
PCT Pub. Date: Jun. 13, 2013

(65) Prior Publication Data
US 2014/0371684 A1  Dec. 18, 2014

Related U.S. Application Data

(60) Provisional application No. 61/567,297, filed on Dec. 6, 2011.

(30) Foreign Application Priority Data

Dec. 6, 2011 (SE) .................. 1151164

(51) Int. Cl.
*A61M 39/20* (2006.01)
*A61J 1/14* (2006.01)
(Continued)

(52) U.S. Cl.
CPC ........... *A61M 5/3204* (2013.01); *A61M 5/3202* (2013.01); *A61M 5/3213* (2013.01);
(Continued)

(58) Field of Classification Search
CPC ............. A61M 2005/3109; A61M 2005/3104; A61M 2005/2488; A61M 2005/2496; A61M 2005/3217; A61M 2005/3219; A61M 5/3202; A61M 5/3216; A61M 5/321; A61M 5/3213; A61J 1/1412; A61J 1/1418; A61J 1/1425; A61J 1/1481; A61J 11/008; B65D 41/04; B65D 41/085; B65D 41/47; B65D 43/0225; B65D 43/0231
See application file for complete search history.

(56) References Cited

U.S. PATENT DOCUMENTS 7,771,397 B1    8/2010  Olson
2010/0268169 A1* 10/2010 Llewellyn-Hyde . A61M 5/2033
                                                          604/192

FOREIGN PATENT DOCUMENTS

GB    242486 A    10/2006
GB   2451663 A    2/2009
(Continued)

OTHER PUBLICATIONS

STIC search report Jun. 23, 2015.*
(Continued)

*Primary Examiner* — Kami A Bosworth
*Assistant Examiner* — Nilay Shah
(74) *Attorney, Agent, or Firm* — Piedmont Intellectual Property

(57) ABSTRACT

The invention relates to an injection device (1) comprising a housing (2) having an abutment surface (5) provided near a proximal end, said abutment surface extending at least partially around a perimeter of said housing and at least one engagement structure (6) provided at the abutment surface, wherein the injection device further comprises: a cap (7) provided with an opening (10) at a distal end (9); wherein a first lifting pole (11) is pivotally arranged within the cap, said first lifting pole being pivotally connected to the cap and being arranged to bear against the abutment surface in a fully attached position on the housing; and wherein relative rotational movement between the cap and the housing around a longitudinal axis will cause a distal end of the first lifting pole to engage with the engagement structure thus causing axial displacement of the cap relative to the housing towards a detached position of the cap.

13 Claims, 3 Drawing Sheets

(51) Int. Cl.
- *A61M 5/32* (2006.01)
- *B65D 41/47* (2006.01)
- *B65D 41/04* (2006.01)
- *A61M 5/31* (2006.01)
- *B65D 43/02* (2006.01)
- *A61M 5/20* (2006.01)

(52) U.S. Cl.
CPC .............. *A61J 1/1412* (2013.01); *A61J 1/1418* (2015.05); *A61J 1/1481* (2015.05); *A61M 5/20* (2013.01); *A61M 5/321* (2013.01); *A61M 2005/3104* (2013.01); *B65D 41/04* (2013.01); *B65D 41/47* (2013.01); *B65D 43/0231* (2013.01)

(56) References Cited

FOREIGN PATENT DOCUMENTS

| | | |
|---|---|---|
| WO | 2005/115508 A1 | 12/2005 |
| WO | 2009/040601 A1 | 4/2009 |
| WO | 2009/040603 A1 | 4/2009 |

OTHER PUBLICATIONS

Sweden Patent Office, Int'l Search Report in PCT/SE2012/051314, Mar. 6, 2013.
Sweden Patent Office, Written Opinion in PCT/SE2012/051314, Mar. 6, 2013.

* cited by examiner

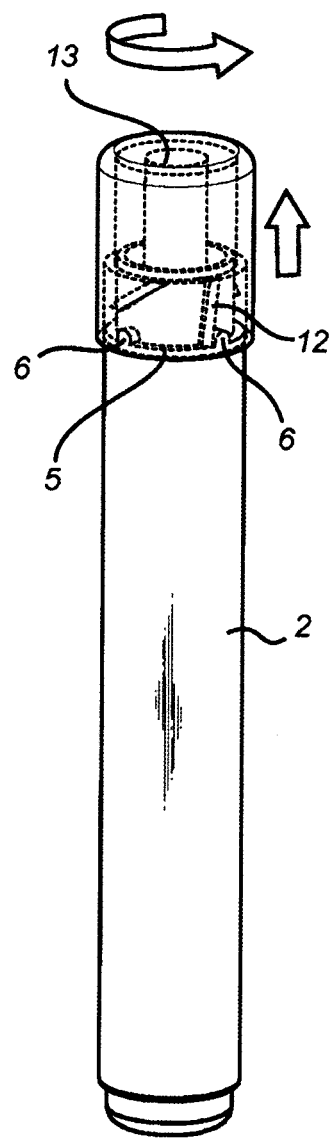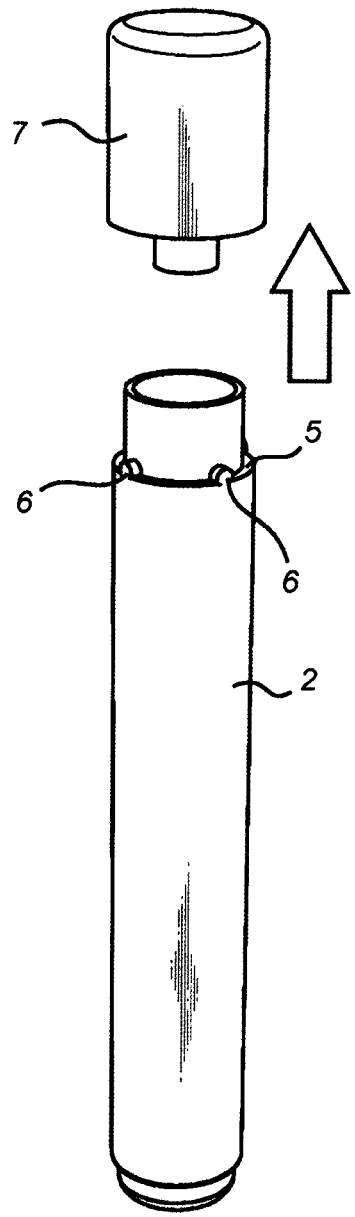
Fig. 2C
Fig. 2D

INJECTION DEVICE

FIELD OF THE INVENTION

The present invention relates to an injection device, especially an injector where the needle is covered by a cap and possibly a needle shield.

BACKGROUND OF THE INVENTION

Injectors for regular use by the patient, such as for example pen injectors and automatic injectors, should preferably be provided with means for covering the needle when the injector is not used to prevent any needle stick injuries. This can for example be done by means of a cap which can be slid onto the injector housing. Often, the needle is kept sterile in a rigid needle shield (RNS) or a flexible needle shield (FNS), which is also covered by the cap. In order to avoid damage to the needle upon retraction of the cap, it is important to avoid any relative rotational movement between the needle shield and the needle. One solution to this problem is to provide the cap and the injector housing with connecting means which prevents a user from rotating the cap during retraction thereof. By doing so, retraction of the cap can only be done by an axial movement of the cap, thus avoiding relative rotational movement between the needle shield and the needle. This has a major drawback in that it can be very hard for some users, e.g. impaired or elderly, to retract the cap with an axial movement.

WO-2009/040601 describes a method where rotational movement of the cap relative to the housing is translated into an axial movement of the cap by helical means. To avoid relative rotational movement between the needle shield and the needle, the needle shield is fixedly mounted within a sheath which in turn is mounted to the cap such that it may rotate relative the cap. Thereby the rotational/axial movement of the cap is translated into an axial movement only of the needle shield.

SUMMARY OF THE INVENTION

It is an object of the invention to provide an injection device with improved characteristics when it comes to the removal of the cap from the housing. This object and other objects are solved by an injection device as claimed in claim 1. Preferred embodiments of the present invention are defined in the dependent claims.

Thus, in accordance with an aspect of the present invention, there is provided an injection device comprising a housing having a distal end and a proximal end. An abutment surface is provided near the proximal end of the housing, said abutment surface extending at least partially around a perimeter of said housing and facing away from said distal end and at least one engagement structure is provided at the abutment surface. The injection device further comprises a cap which is removably attached to said proximal end of the housing. The cap has a proximal end and a distal end and is provided with an opening at said distal end, wherein internal dimensions of said opening correspond to the outer dimensions of the proximal end of the housing to allow said cap to be slipped onto the proximal end of the housing. Within the cap a first lifting pole is pivotally arranged and pivotally connected to the cap at a proximal end by a pivotal connection. The first lifting pole is arranged to bear against the abutment surface at a distal end when the cap is in a fully attached position on the housing and the first lifting pole extends from the abutment surface to the pivotal connection to the cap along an axis which is inclined in relation to a longitudinal axis of the housing when the cap is in said fully attached position. Relative rotational movement between the cap and the housing in a first direction around said longitudinal axis will cause the distal end of the first lifting pole to engage with the engagement structure and bring about an alignment of the first lifting pole with the longitudinal axis of the housing thus causing axial displacement of the cap relative to the housing towards a detached position of the cap. When turned in a first direction, the lifting pole will slide over the abutment surface until the distal end, which in this case is also the leading end of the first lifting pole, reaches an engagement structure. The motion of the distal, leading end of the first lifting pole will come to a standstill and a continued rotation of the cap relative to the housing will force the first lifting pole to straighten and become parallel with the longitudinal axis of the housing and the cap thereby creating an axial movement of the cap relative to the housing. The construction with a lifting pole provides a number of advantages. It is for example possible to adjust the force necessary to loosen the cap from the housing by using a lifting pole of suitable length. Due to the relationship between the lever arms, a shorter lifting pole will provide a user with a stronger lever but a shorter total length of stroke. In many cases, the total length of stroke is of less relevance since the main problem for a user is to achieve an initial disengagement of the cap from the housing, for instance to tear off a sealing or overcome internal friction. As soon as this is done, the removal of the cap is unproblematic. If, on the other hand, a longer total length of stroke is of importance, the lifting pole can be made longer.

In accordance with an embodiment of the injection device, a second lifting pole is provided. By providing a second lifting pole it is possible to achieve an axial displacement of the cap irrespective of the rotational direction of the cap relative to the housing. Also, an advantageous distribution of the forces can be obtained by using two lifting poles.

In accordance with an embodiment of the injection device, the first and the second lifting pole extend along axes which are positively resp. negatively inclined to the longitudinal axis of the housing when the cap is in said fully attached position. This assures that a cap can be removed from the housing irrespective of the rotational direction of the cap relative to the housing. As described above, when turned in a first direction, the lifting poles will slide over the abutment surface until a distal and leading end of one of the lifting poles reaches an engagement structure. If, during the rotation a distal but trailing end of the other lifting pole reaches an engagement structure first, this lifting pole will, due to the pivotal arrangement, slide past the engagement structure and the rotational movement can proceed until a distal and leading end of a lifting pole reaches an engagement structure and the axial movement of the cap takes place.

In accordance with an embodiment of the injection device, two pairs of lifting poles are provided. Each pair comprises a first and a second lifting pole. This construction ensures independence of rotational direction as well as favorable distribution of forces.

In accordance with an embodiment of the injection device, the pivotal connections of the lifting poles are arranged to bias the lifting poles towards said positively resp. negatively inclined positions. By providing the pivotal connection of the lifting poles with a slight bias, it can be ensured that the lifting poles adopt their initial inclination towards the longitudinal axis of the housing 2 in order to ensure independence of rotational direction if the cap is replaced on the injector housing. This is particularly convenient when the injector is a multi-use injector since the user friendliness can be maintained for each use.

In accordance with an embodiment of the injection device, a needle shield for receiving a needle is attached to the cap. A needle shield, rigid or flexible, can be attached to the cap in order to ensure that the needle is kept sterile.

In accordance with an embodiment of the injection device, the needle shield is rotatably mounted to the proximal end of the cap. This has the advantage that the needle shield does not rotate with the cap during the extraction from the housing. Such relative rotational movement between the needle and the needle shield may be detrimental for the needle.

In accordance with an embodiment of the injection device, the lifting poles are moulded into the cap. It is possible to mould the lifting poles directly into the cap. This is cost effective and time saving.

In accordance with an embodiment of the injection device, the abutment surface extends around the whole perimeter of said housing and a plurality of engagements structures are provided on the abutment surface and evenly distributed along the perimeter of the housing.

In accordance with an embodiment of the injection device, the engagement structures comprise protrusions extending from the abutment surface in a direction away from the distal end of the housing.

In accordance with an embodiment of the injection device, the engagement structures comprise recesses in the abutment surface.

In accordance with an embodiment of the injection device, the injection device is a disposable injector.

In accordance with an embodiment of the injection device, the injection device is a reusable injector.

BRIEF DESCRIPTION OF THE DRAWINGS

FIG. 2c is a perspective view of an embodiment of the invention with the cap in a detached position.

FIG. 2d is a perspective view of an embodiment of the invention with the cap in a removed position.

DESCRIPTION OF PREFERRED EMBODIMENTS

Embodiments of the present invention will now be described in detail. As should be noted in the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

Figure 1:
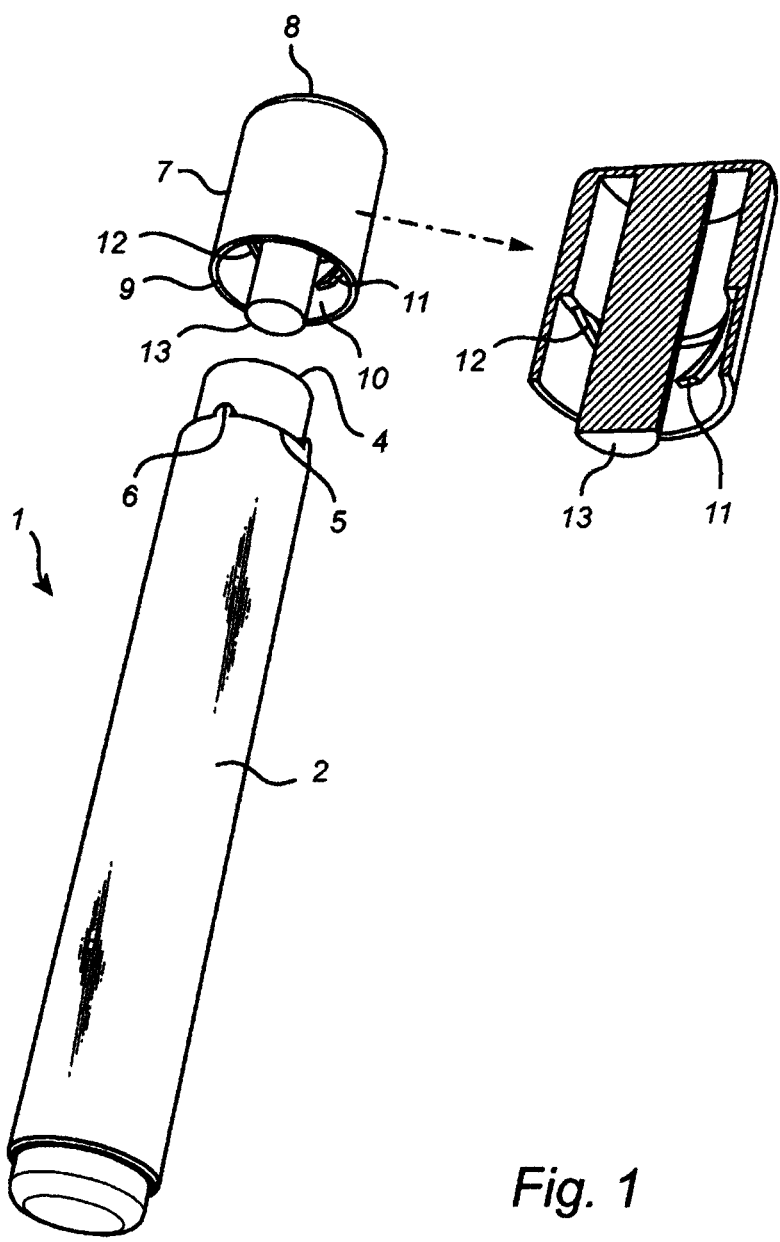
FIG. 1 shows a perspective view of an embodiment of the invention as well as a cut-open perspective view.

In an embodiment of an injector of the invention, as shown in the figures, the injector comprises a housing 2. Within the housing, a container such as a syringe with an injection needle and a drive mechanism for expelling an amount of a product, such as a medicament, is provided. For reasons of simplicity, only the outer housing is shown in the figures. The housing 2 has a distal end 3 and a proximal end 4. Near said proximal end 4 an abutment surface 5 is provided which in this embodiment extends around the full perimeter of the housing 2. An abutment surface which does not extend around the full perimeter of the housing 2 is of course also imaginable, as well as a plurality of abutment surfaces 5 distributed around the perimeter of the housing 2. Evenly distributed engagement structures 6 are provided on the abutment surface 5, indicated by 15. The engagement structures 6 can be of any suitable number; in this embodiment four engagement structures 6 are provided, of which two can be seen in the figures. Also shown in FIG. 1 is a cap 7. Cap 7 covers and protects the injection needle prior to use of the injector 1. The cap 7 has a proximal end 8 and a distal end 9 and is provided with an opening 10 at said distal end 9. The internal dimensions of the opening 10 correspond to the outer dimensions of the proximal end 4 of the housing 2 such that the cap 7 can be slipped onto the housing 2. A needle shield 13 is indicated in the figures, this needle shield may for example be a Rigid Needle Shield (RNS) or a Flexible Needle Shield (FNS) known in the art. Advantageously, the needle shield 13 is rotatably mounted within the cap 7 such that the needle shield 13 and the cap 7 may rotate relative to each other. Thereby it is possible for the needle shield 13 to only perform an axial movement during displacement of the cap 7 even though the cap 7 itself performs a combined axial and rotational movement during detachment. This is favourable, since relative rotational movement between the needle and the needle shield 13 may be detrimental for the needle. Also shown in the FIG. 1 are the lifting poles 11, 12 of the present invention. These lifting poles 11, 12 are pivotally arranged within the cap and their interaction with the abutment surface 5 and the engagement structures 6 will be thoroughly described below in connection with FIGS. 2a-2d.

Figure 2A:
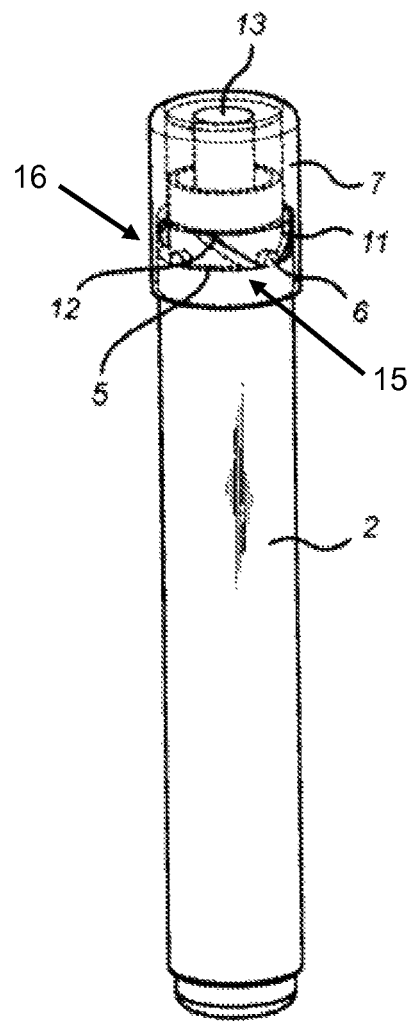
FIG. 2a is a perspective view of an embodiment of the invention with the cap in a fully attached position
Figure 2B:
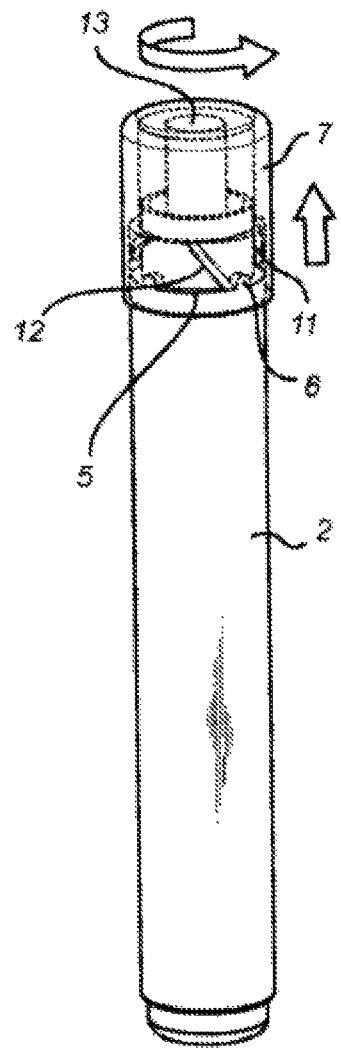
FIG. 2b is a perspective view of an embodiment of the invention with the cap in a partly detached position.

FIG. 2a shows an injector 1 according to the present invention where the cap 7 is in a fully attached position on the housing 2. In this figure, the cap 7 is shown in a position where two lifting poles 11, 12 are located one on each side of an engagement structure 6. The lifting poles 11, 12 extend from the abutment surface 5 towards a pivotal connection indicated by 16 to the cap 7 along an axis which is inclined to the longitudinal axis of the injector 1. Preferably, two lifting poles 11, 12 are provided where one lifting pole is positively inclined to the longitudinal axis of the injector 1 and the other lifting pole is negatively inclined to the longitudinal axis of the injector 1. This has the advantageous that the cap 7 can be detached independently from the rotational direction. Even more advantageous is to provide two pairs of lifting poles 11, 12, one pair opposite of the other. Thereby independence of the rotational direction is achieved and the cap is axially displaced without unnecessary friction due to uneven load distribution. A single pole is however sufficient to achieve the objections of the present invention. Starting from this position, a user holds the housing 2 with one hand and grasps the cap 7 with her/his other hand and rotates the cap 7 and housing 2 in opposite directions. Alternatively rotates one part, i.e. either the cap 7 or the housing 2, while just holding the other part in position. The result of an initial relative rotational movement between the cap 7 and the housing is shown in FIG. 2b. Due to the rigidity of the lifting pole 11, and possibly further lifting poles on the rear side, not shown in FIG. 2b, and the fact that the lifting poles are pivotally connected to the cap, the relative rotation between the cap 7 and the housing 2 will force the lifting pole 11 towards a position which is less inclined to the longitudinal axis of the housing 2. This straightening of the lifting pole 11 leads to an axial movement of the cap 7 relative the housing 2 towards a detached position of the cap 7. If the relative rotation between the cap 7 and the housing 2 is continued, the position shown in FIG. 2c will be the result. Here, the lifting pole 11 is completely straightened out and parallel with the longitudinal axis of the injector 1.

The cap 7 is now more or less detached from the housing 2 and can easily be removed from the housing, as shown in FIG. 2d.

Finally, it is realized, that an injection device according to the invention has a number of advantages over the known prior art devices. The properties of the detachment of the cap 7 can be adjusted by correct dimensioning of the different parts of the injector. For example, it is often the case that it is the initial loosening of the cap that is the most troublesome to a user. The injector may for example be provided with a sealing that has to be broken. Also, the internal friction between the cap 7 and the housing 2 is often higher at an initial stage of the detachment than towards the end. In these cases, it could be advantageous to provide lifting poles with a reduced length. The shorter the lifting poles are, while still being long enough to be inclined to the longitudinal axis of the injector 1 when the cap is in a fully attached position, the stronger the lifting force at an initial stage will be. A shorter lifting pole will of course offer a reduced stroke length, but as the initial detachment often is the hardest part, this is of less relevance. There are, however, cases where a higher force contribution is needed at a later stage of detachment. For example, it is possible that the system with a cap 7 having a needle shield 13 has a built-in play such that during an initial stage of detachment, less force contribution is necessary and then, as the built-in play has been overcome, a higher force contribution might be desirable later during detachment. This also calls for a longer stroke length in order to provide sufficient detachment. This is achieved by providing longer lifting poles. The lifting poles 11, 12 in FIGS. 1 and 2a-2d are provided with opposite inclinations towards the longitudinal axis of the injector 1, thus making the direction of rotation irrelevant. In FIG. 2a, showing the initial, fully attached position of the cap 7, the lifting poles 11, 12 are positioned immediately adjacent engagement structure 6 such that any relative rotation between the cap 7 and housing 2 will cause axial displacement of the cap 7 relative to the housing 2. The initial position of the lifting poles 11, 12 along the abutment surface is, however, irrelevant for the functioning of the present invention. If two lifting poles 11, 12 are positioned on the abutment surface 5 between two engagement structures 6, a user simply has to rotate the cap 7 relative to the housing 2 a bit further. This will cause a leading lifting pole to simply slide over the engagement structure 6 and immediately thereafter a trailing lifting pole will engage with the engagement structure 6 and the detachment of the cap 7 will commence. This is possible due to the pivotal connection of the lifting poles and is especially relevant if the present invention is used with a reusable injector. This means that a user does not have to put the cap 7 back on the housing in a certain position but can rather just re-attach it in any position. Further, especially if the present invention is used in connection with a reusable injector, it would be advantageous to provide the pivotal connection of the lifting poles 11, 12 with a bias such that they return to their initial inclination towards the longitudinal axis of the injector 1 such that the independence from the rotational direction of the cap 7 relative to the housing 2 can be maintained for following detachments. In case of single use injectors, this is of course not quite as relevant. Even though the engagement structures 6 are shown in the figures as separate protruding elements provided on the abutment surface 5, it is of course also possible that they constitute a major part of the perimeter of the housing such that the abutment surface only comprises the bottom of one or more recesses, e.g. a ratchet surface or a toothed surface. As long as the lifting poles can be positioned therein and brace against it during detachment of the cap. Further, even though the lifting poles are indicated to form part of the cap whereas the abutment surface and the engagement structures form part of the housing of the injection device, the opposite arrangement is of course also possible and lies within the scope of the present invention. This would mean that lifting poles are provided on the housing of the injection device and an abutment surface with engagement structures is provided within the cap.

It is to be understood that the embodiments described above and in the drawings are to be regarded only as non-limiting examples of the invention and that they may be modified in many ways within the scope of the claims.

The invention claimed is:

1. An injection device, comprising:
   a housing having a distal end and a proximal end and an abutment surface provided near the proximal end of the housing, the abutment surface extending at least partially around a perimeter of the housing and facing away from the distal end and at least one engagement structure provided at the abutment surface;
   a cap removably attached to the proximal end of the housing and having a proximal end and a distal end with an opening at the distal end of the cap, wherein internal dimensions of the opening correspond to outer dimensions of the proximal end of the housing, thereby allowing the cap to slip onto the proximal end of the housing;
   and a first lifting pole pivotally arranged within the cap, the first lifting pole being pivotally connected to the cap at a proximal end of the first lifting pole by a pivotal connection and being arranged to bear against the abutment surface at a distal of the first lifting pole when the cap is in a fully attached position on the housing; wherein the first lifting pole extends from the abutment surface to the pivotal connection to the cap along an axis inclined relative to a longitudinal axis of the housing when the cap is in the fully attached position;
   wherein relative rotational movement between the cap and the housing in a first direction around the longitudinal axis causes the distal end of the first lifting pole to engage with the at least one engagement structure and alignment of the first lifting pole with the longitudinal axis of the housing, thereby causing axial displacement of the cap relative to the housing toward a detached position of the cap.

2. The injection device of claim 1, further comprising a second lifting pole.

3. The injection device of claim 2, wherein the first and second lifting poles extend along axes, one of which is positively inclined to the longitudinal axis of the housing and the other of which is negatively inclined to the longitudinal axis of the housing when the cap is in the fully attached position.

4. The injection device of claim 3, comprising two first and two second lifting poles.

5. The injection device of claim 3, wherein pivotal connections of the first and second lifting poles are arranged to bias the first and second lifting poles respectively toward positively and negatively inclined positions.

6. The injection device of claim 2, wherein the first and second lifting poles are molded into the cap.

7. The injection device of claim 1, further comprising a needle shield for receiving a needle attached to the proximal end of the cap.

8. The injection device of claim 7, wherein the needle shield is rotatable in relation to the cap.

9. The injection device of claim 1, wherein the abutment surface extends around the whole perimeter of the housing, and a plurality of the engagement structures are provided on the abutment surface evenly distributed along the perimeter of the housing.

10. The injection device of claim 9, wherein the engagement structures comprise protrusions extending from the abutment surface in a direction away from the distal end of the housing.

11. The injection device of claim 9, wherein the engagement structures comprise recesses in the abutment surface.

12. The injection device of claim 1, wherein the injection device is a disposable injector.

13. The injection device of claim 1, wherein the injection device is a reusable injector.

* * * * *